United States Patent [19]

Barber

[11] 4,232,662

[45] Nov. 11, 1980

[54] THERAPEUTIC DEVICE FOR A HUMAN BODY

[76] Inventor: S. Morgan Barber, P.O. Box 223, Yerington, Nev. 89447

[21] Appl. No.: 958,013

[22] Filed: Nov. 6, 1978

[51] Int. Cl.[3] .......... A61F 5/00

[52] U.S. Cl. .......... 128/71; 272/144

[58] Field of Search .......... 272/144, 145; 128/24 R, 128/71, 72, 73, 74

[56] References Cited

U.S. PATENT DOCUMENTS

| | | | |
|---|---|---|---|
| 3,081,085 | 3/1963 | Girolamo | 272/145 X |
| 3,286,708 | 11/1966 | Gartner | 272/145 X |
| 3,568,669 | 3/1971 | Stites | 128/71 |
| 4,114,613 | 9/1978 | Kuhn | 128/71 X |

FOREIGN PATENT DOCUMENTS

| | | | |
|---|---|---|---|
| 1390536 | 4/1975 | United Kingdom | 272/144 |

*Primary Examiner*—John D. Yasko

*Attorney, Agent, or Firm*—Paul A. Weilein; B. F. Spencer

[57] ABSTRACT

A therapeutic device for treating and exercising the human body by tilting it to different angular positions. The device has a body supporting structure that is pivotally supported on a main frame, the body supporting structure being comprised of an upper body supporting portion and a lower body supporting portion, these portions being interconnected by a central elongate frame. The upper body supporting portion includes an elongate platform. The lower body supporting portion includes a first support in the form of step members arranged to extend under each foot and form a support to limit endwise movement of the body in a downward direction when the body supporting structure is tilted so as to elevate the head of the body thereon above a horizontal position, and a second support positioned and operative to embrace each ankle area and adjacent foot instep area in a manner to form a support to limit endwise movement of the body in an opposite downward direction when the body supporting structure is tilted so as to lower the head of the body below a horizontal position. A variety of unique adjustments are provided for varying the relationship between the components of the first support and the second support in order to obtain a maximum degree of comfort during use of the device.

18 Claims, 15 Drawing Figures

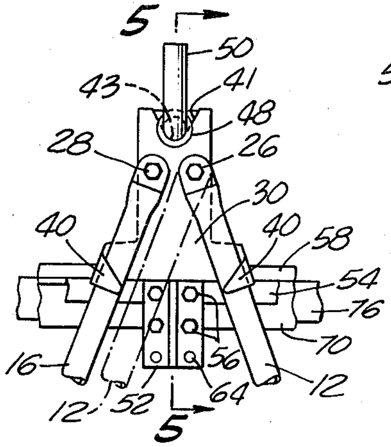
FIG. 4.
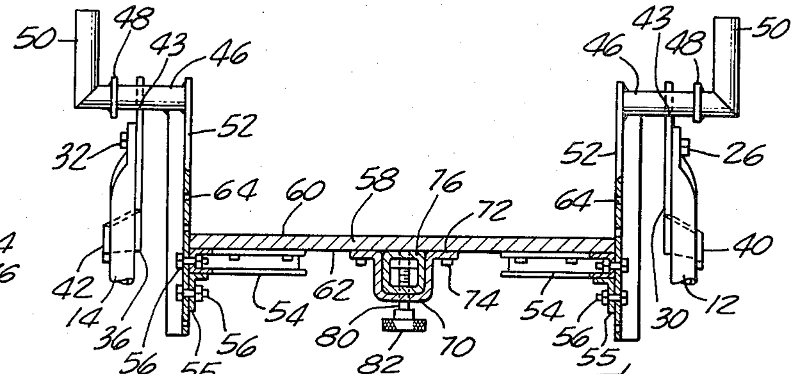
FIG. 5.
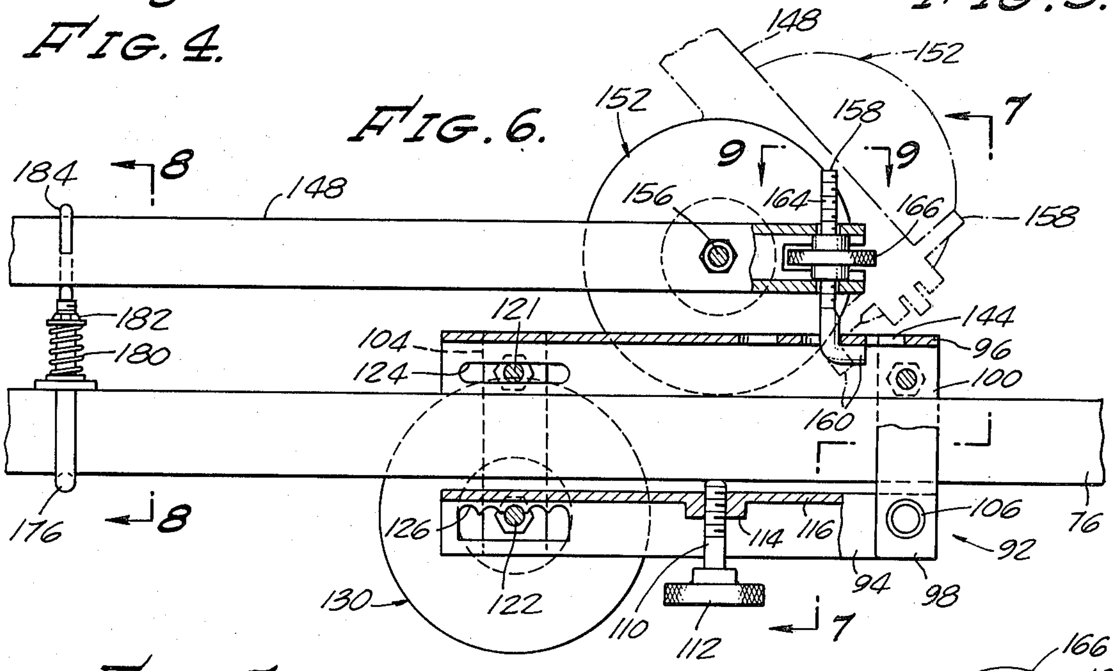
FIG. 6.
FIG. 7.
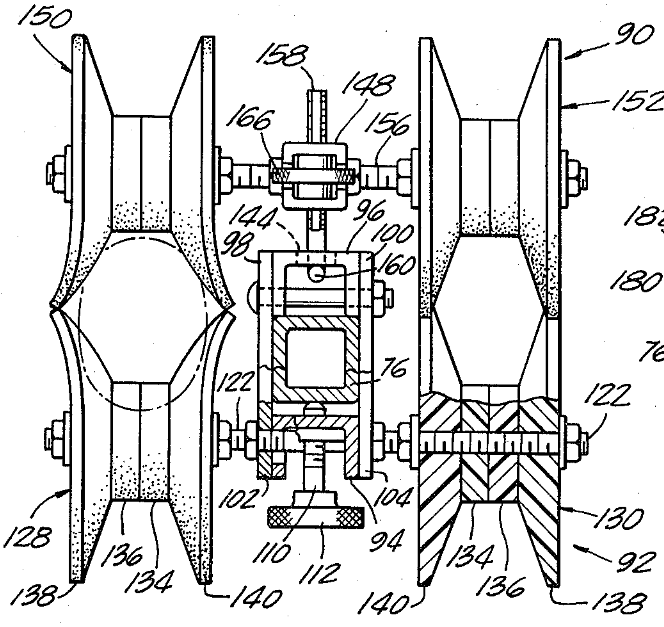
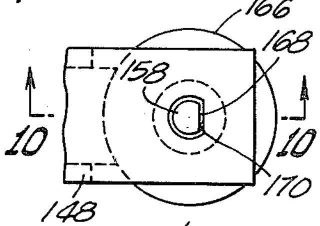
FIG. 9.
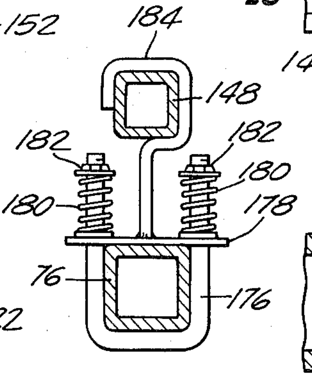
FIG. 8.
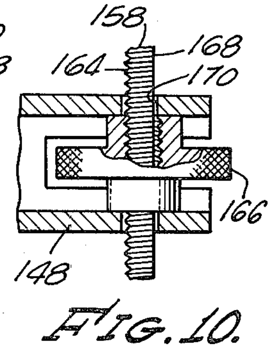
FIG. 10.

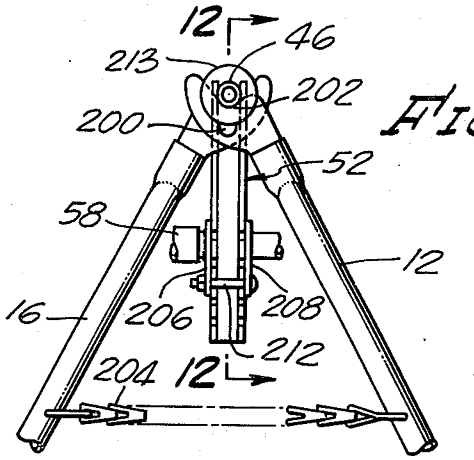
FIG. 11.
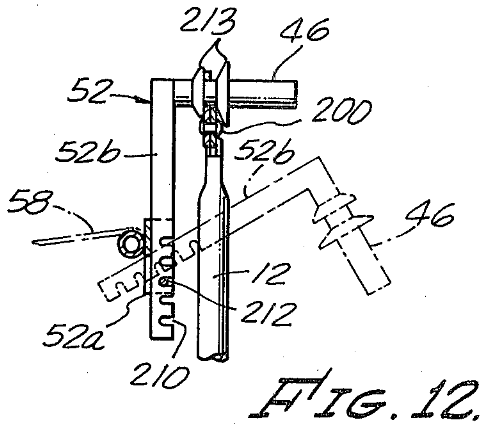
FIG. 12.
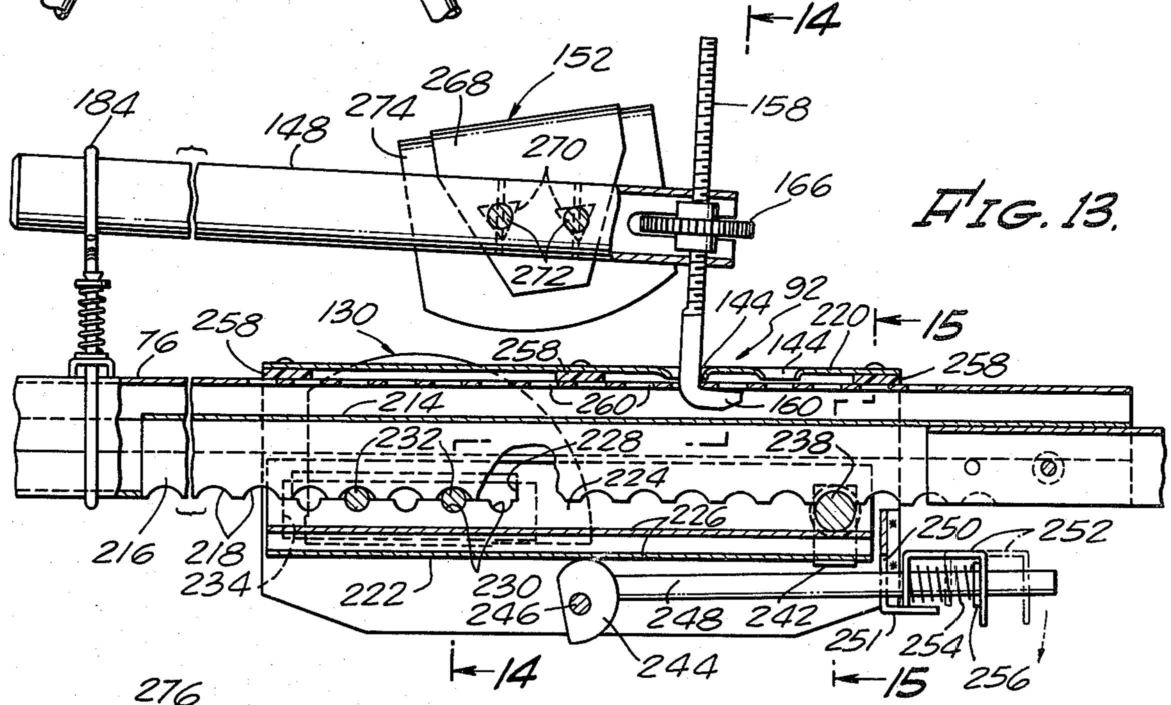
FIG. 13.
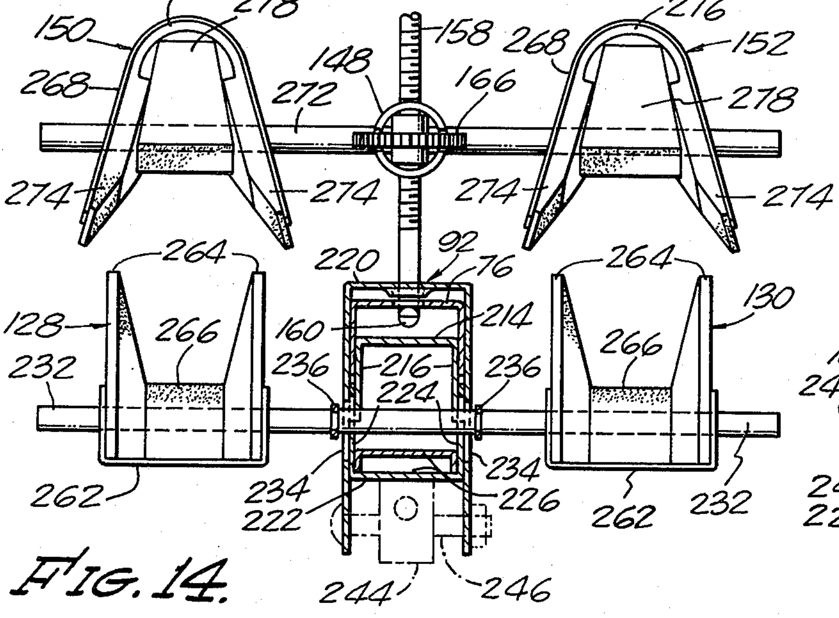
FIG. 14.
FIG. 15.
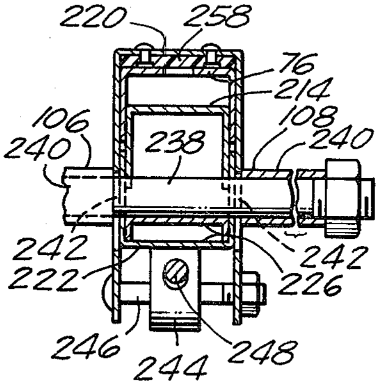

THERAPEUTIC DEVICE FOR A HUMAN BODY

BACKGROUND OF THE INVENTION

The present invention relates generally to devices for the therapeutic treatment and exercising of the human body.

It has heretofore been generally known that certain types of body exercising and treatment devices, if properly designed and operated, can produce desirable and healthful therapeutic results upon the human body. In this category, devices for moving the human body between upright and inverted positions have been found to be particularly beneficial. Supporting the human body in an inverted position from the lower limbs tends to produce a lengthening of the body; separate the joint spaces, especially the intervertebral joint spaces; aid in the elimination of vascular and visceral ptosis; to decompress the body; to aid circulatory exchange; and to readjust the lines of stress of the body.

A variety of devices have heretofore been known in which a body could be moved from upright to inverted positions and even continuously rotated. Typical of the prior art devices are those disclosed in the Heisler et al U.S. Pat. No. 3,152,802 and the Gartner U.S. Pat. No. 3,286,708.

The prior art devices differ primarily in the structural design of the parts for embracing and holding the lower body extremities to permit the body inversion, and while such function is in general realized, the prior art devices have, in the main, embodied inherent disadvantages as well as problems attending their use. For example, in a number of these devices it was difficult for one person to use the device without the assistance of another person to aid in placement of the body in the device and in the engagement of the lower body supporting means. In other of the devices it was difficult for the user to tilt or rotate the body supporting structure without assistance.

One of the most prominent difficulties of the prior art devices resides in the inability of the holding means for the lower extremities to hold these extremities comfortably for extended periods of time, or to be able to effectively engage the lower extremities in a manner to prevent undesirable slippage during transitional movements of the body supporting structure between body upright and body inverted positions.

SUMMARY OF THE INVENTION

More particularly, the present invention is concerned with the provision of an improved therapeutic device which can be operated with ease and without assistance to support and move the human body between upright and inverted positions, and in which the holding means for the lower extremities may be conveniently accessible to the user for movement into engaged and disengaged positions, and for the making of the necessary adjustments to properly balance the body on the body supporting structure, and tiltingly change the body position at will.

With the foregoing in mind, it is one object of the herein described invention to provide an improved therapeutic device by means of which an unskilled person can support and move his body through tilting movements between an upright position and an inverted position.

A further object is to provide a device for the foregoing purpose which is economical of manufacture, which can be easily disassembled and stored, and which embodies adjustments whereby it may be easily and readily accommodated to the variants of sizes of the human body.

Another object of the invention is to provide in a therapeutic device of the type in which the body is tilted into inverted positions, improved holding means for the feet and ankle portions of the body, which provide a cushion support, and which may be easily adjusted to fit the user's extremities, whereby these extremities will be comfortably embraced and held during lengthy periods of body inversion.

Still another object is to provide improved means for orienting the body on the body supporting structure so as to properly position the center of gravity of the body in a balanced relationship to the pivotal support of the body supporting structure, to the end that the user may vary the tilted position of the body supporting structure merely by extending his arms in different directions.

A still further object resides in the provision of improved means for embracing the ankle and instep portions of the user's body, and in which the embracing elements may be releasably locked by the user in their operative positions and easily released to permit the user to dismount from the device.

Further objects and advantages of the invention will be brought out in the following part of the specification, wherein detailed description is for the purpose of fully disclosing a preferred embodiment of the invention without placing limitations thereon.

BRIEF DESCRIPTION OF THE DRAWINGS

Referring to the accompanying drawings, which are for illustrative purposes:

FIG. 4 is a fragmentary side view illustrating the pivotal connection between the body supporting structure and the main frame;

FIG. 5 is a fragmentary transverse sectional view of the same, taken substantially along line 5—5 of FIG. 4;

FIG. 6 is an enlarged fragmentary side view of the lower body supporting portion shown in FIG. 3;

FIG. 7 is an end view, partially in cross section, of the lower body supporting portion, taken substantially along the line 7—7 of FIG. 6;

FIG. 8 is a sectional view taken substantially along the line 8—8 of FIG. 6, showing details of means for locking the lower body supporting portion in an operative position;

FIG. 9 is a fragmentary plan view of the locking means as seen along the line 9—9 of FIG. 6;

FIG. 10 is a fragmentary sectional view, taken substantially on line 10—10 of FIG. 9;

FIG. 11 is a view similar to FIG. 4 of a modified form of the invention;

FIG. 12 is a fragmentary sectional view taken substantially on line 12—12 of FIG. 11;

FIG. 13 is an enlarged fragmentary side view similar to FIG. 6, partly in section, of the lower body supporting portion of the modified form of the invention;

FIG. 14 is a view similar to that of FIG. 7, and including a transverse section taken substantially on line 14—14 of FIG. 13; and FIG. 15 is a fragmentary transverse sectional view taken substantially on line 15—15 of FIG. 13.

DESCRIPTION OF THE SEVERAL EMBODIMENTS

Figures 1, 2, 3:
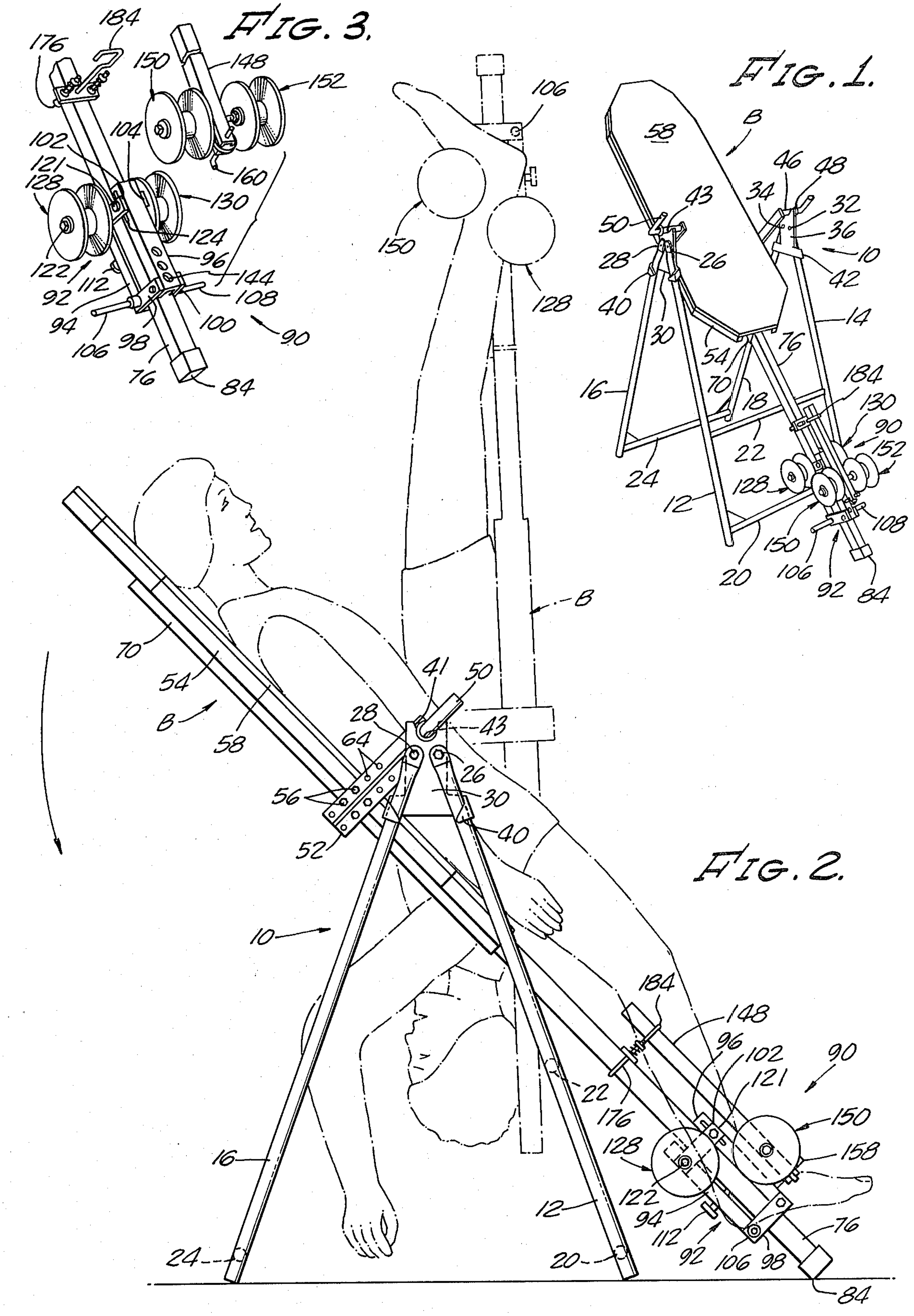
FIG. 1 is a perspective view of a therapeutic device according to the present invention.
FIG. 2 is an enlarged side elevational view illustrating several operative positions of the device.
FIG. 3 is a fragmentary exploded perspective view, showing means for supporting and securing the lower portions of the body therein.

Referring more specifically to the drawings, for illustrative purposes there is shown in FIG. 1 a therapeutic device, as generally indicated by the numeral 10, embodying the features of the present invention. More specifically, the device comprises a body supporting structure B that is pivotally mounted for rotational swinging movement on a main supporting A-frame formed of two forward legs 12 and 14 and two rearward legs 16 and 18. The legs 12, 14 have a connecting crossbar 20 extending therebetween, and also a connecting crossbar 22 which is in the swinging path of movement of the body supporting structure B and provides a stop for limiting such swinging movement in one direction. Rear legs 16 and 18 have a transverse bottom connecting crossbar 24. The legs 12 and 16 are independently pivotally engaged at 26 and 28 to a pivot support plate 30, and similarly the legs 14 and 18 are pivotally secured at 32 and 34 to a pivot support plate 36 on the other side of the frame. The two sets of legs are adapted to be positioned for use, as shown in full lines in FIG. 4, and moved together as shown in phantom lines for storage. Spreading of the legs into their use position is limited by stops 40 and 42 on the plates 30 and 36, respectively.

As best seen in FIGS. 1, 2, 4 and 5, the top edges of the support plates 30 and 36 are respectively formed with a notch 41 having an arcuate bottom surface 43, in which supporting side trunnions 46 of the body supporting structure B are adapted to pivot. The body supporting structure B is laterally retained in a proper operating position between the plates 30 and 36 by means of outwardly disposed abutment flanges 48. Also, as shown, the outer ends of the trunnions, if desired, may be formed to provide handles 50 which are in a position for easy grasp by a user on the body supporting structure, if desired.

The side trunnions 46 at their inner ends are connected with opposed downwardly extending bracket members 52, which are positioned on opposite sides of a platform 58 that forms an upper body supporting portion of the body supporting structure B. Each side of this platform is reinforced by an edge channel 54 secured to its underside. Intermediate its ends, the platform is secured on each side to the bracket members 52 by means of retaining bolts 56 having securing engagement with the adjacent channel 54 and an underlying reinforced angle member 55. The platform 58 has a body-receiving upper side 60 opposite underside 62. The position of the platform 58 in relation to the trunnions 46 is adjustable, and it can be mounted more closely to or farther away from the trunnions simply by repositioning the bolts 56 in the bolt holes 64 provided in the support members 52 for this purpose, as shown in FIGS. 4 and 5.

The upper body supporting portion of the structure B is connected with a lower body supporting portion by means of an interconnection that includes a longitudinally extending channel 70 disposed on the underside of the platform and secured thereto by means of retaining bolts engaged with side flanges 72 formed along the opposite sides of the channel. A central frame member 76 in the form of a rectangular rod or bar is slidably supported in the channel 70, and is arranged to be secured in a longitudinally adjusted position with respect to the platform by means of a bolt 80 having a finger actuator knurled portion 82, the bolt being threadedly engageable through the channel 70 and the frame member 76 in one of a plurality of tapped bores. The frame member 76 is adjusted so that its lower end 84, FIG. 2, will engage the floor or other surface on which the device is placed, and thus serves to limit the tilting movement of the body supporting structure B in a direction opposite to that in which the stop bar 22 is engaged.

The lower body supporting portion, as generally indicated by numeral 90, is carried by the frame member 76, and will now be described with particular reference to FIGS. 1-3 and 6-10. A frame structure generally designated as 92, is slidably supported on the frame member 76 and is comprised of a downwardly opening channel 94 extending along and below the frame member 76, and an upper channel member 96 supported above frame member 76. The channel members are secured together by a pair of bolted side plates 98 and 100 at their outer ends, and side plates 102 and 104 at their inner ends.

One of the bolts for the plates 98 and 100 provides a pivot for the channel 94 and also extends outwardly on the opposite sides of the frame structure 92 so as to form foot engageable step members 106 and 108 respectively on opposite sides of the frame member 76. From the foregoing, it will be apparent that the position of these step members will determine the balancing position of the center of gravity of the body being supported with respect to the pivoting trunnions 46. Also, due to varying body lengths, it is desirable to permit adjustment of the position of these steps. For this purpose, the frame 92 is slidably adjustable along the frame member 76 and adjustably secured in place by a retaining bolt 110 having a finger actuator portion 112, the bolt being threadedly engaged in a boss 114 extending from channel base 116 of the channel 94, whereby its innermost end may be forced against the underside of the frame member 76 at the adjusted position.

The plates 102 and 104 are secured to the channels 96 and 94 by bolts 121 and 122, FIGS. 6 and 7. The upper bolt 121 extends through opposing aligned slots 124 in the side walls of the channel 96 and the lower bolt 122 is adapted to be selectively fitted into one of a plurality of downwardly opening semicircular notches 126 in the side walls of the channel 94. The plates 102 and 104 and the bolts may be changed to adjust their position towards or away from the foot steps 106 and 108 by loosening the bolt 110 so as to permit limited swinging movement of the channel 94 about its pivoted end to a notch disengaged position, whereupon the bolts 121 and 122 may be shifted to the desired new position and the bolt 110 again tightened to seat the bolt 122 in the selected holding notch at the new position.

The lower bolt 122, FIG. 7, extends substantially beyond the opposite sides of channel 94 and provides a support for ankle area engaging members 128 and 130, each comprised of abutting central cylindrical members 134 and 136 and outer wall portions 138 and 140, the wall portions respectively abutting the inner cylindrical portions. The wall portions preferably taper outwardly from the cylindrical inner portions to form, in effect, a circumferentially extending groove surface of engagement. The walls and cylindrical portions are retained in assembled relation on bolt 122 by appropriate nuts shown in FIG. 7. The walls and cylindrical portions are formed of soft resilient plastic or elastomeric material which embrace the ankle area and provide a cushion support therefor. Adjustment of bolts 121 and 122 toward or away from the step members 106 and 108, as previously described, enables the members 128 and 130 to be properly positioned so as to comfortably engage the rear of the lower leg or ankle area above the bottom of the foot, and so as to overlap the area of the lower leg adjacent both sides of each ankle.

The base wall of the channel 96, FIGS. 3 and 6, has a plurality of longitudinally spaced openings 144 for making adjustable connections with a lever 148 which supports a pair of spaced instep and ankle area engaging members 150 and 152, which are of the same construction and material as the ankle area engaging devices 128 and 130. It will be appreciated that while the members 128, 130, 150 and 152 have been shown as circular, these members may be of arcuate configuration. As best seen in FIGS. 6 and 7, the members 150 and 152 are fixed in place on opposite sides of the lever 148 adjacent its outer end by means of a bolt 156, extending through the lever member, and a plurality of appropriate nuts for tightening the members on the bolt and the bolt on the lever member. As thus arranged, the members 150 and 152 will be positioned between and above the step members 106, 108 and the members 128 and 130 with which they will coact to snugly and effectively embrace the ankle and instep areas and form a cushion holding support during tilting movements of the body.

In order to obtain maximum comfort, a variety of adjustments have been provided in order to accommodate the ankle and instep embracing members to the varied sizes and contours in body structures. To this end, the lever 148 is adjustably secured to the frame 92 by means of an L-shaped hooking member 158, FIGS. 6, 7, 9 and 10, having a lower L-leg hook 160 which is adapted to be selectively inserted into one of the openings 144 in the channel 96, as shown in phantom lines in FIG. 6. Such adjustment may be readily accomplished by a user while standing on the step members 106 and 108, since the lever member 148 is in convenient operating reach for disconnection, adjustment and reconnection.

The upper leg of the hooking member 158 has threads 164 engaged in an adjusting knurled nut 166 which is rotatably confined within the lever member 148. The upper leg is formed with a flat surface 168, FIGS. 9 and 10, which is adapted to engage a flat portion 170 on the lever member 148 to prevent rotation of the member 158. Thus, by rotation of the knurled nut 166 the operative position of the members 150 and 152 carried by the lever 148 may be preadjusted so as to be closer or farther away from the members 128 and 130 and the step members 106 and 108.

As best shown in FIGS. 1 and 6–8, unique means are provided for releasably locking the lever 148 in its operative position in which it extends in generally spaced parallel relation along the frame member 76 (FIG. 6). For such purpose, an upstanding bail 184, shaped to slip endwise over the outer end of the lever 148, is slidingly and resiliently retained on the frame member 76 for movement therealong. More specifically, the bail has a base end which is welded or otherwise secured to a transverse bridging bar 178 positioned to engage one side of the frame member 76. An attaching U-bolt 176 embraces the frame member 76 and has threaded legs which extend through end apertures in the bridging bar and are fitted with compression coiled springs 180 having one end bearing against the bar and their other end bearing against an abutment washer engaged by a nut 182 in each case. The bail may be readily moved along the frame member to released and locking positions with respect to the lever 148, and in the released position permits the user of the device to conveniently swing the lever to a released detached position with respect to the frame 92 to release the ankle holding means, or readjust the members 150 and 152, or for other reasons.

After the lever 148 has been secured in its operative position by the bail, the feet are in the position as shown in full lines in FIG. 2, wherein the body will be supported against endwise movement primarily by the step members 106 and 108. If the ankle and instep engaging members are in a proper and comfortable adjustment, the user may then pivotally swing the body supporting structure B to the body inverted position shown in phantom lines in FIG. 2, wherein endwise movement of the body will be primarily opposed by the coaction of members 128, 130 and 150, 152, since the step members 106 and 108 are now disengaged from the feet. With the body properly balanced on the body supporting structure B, the pivotal movements thereof may be controlled simply by movements of the arms to differently oriented outstretched positions.

The therapeutic device of the present invention, as described above, is simple and easy to use and adjust. In order for the user to place his body on the body supporting structure B, the structure should be placed in position, as shown in FIG. 1. By then releasing the bail 184, the lever 148 is swung to the release position as shown in phantom lines, FIG. 6, which will enable its detachment together with the members 150 and 152, from the frame 92. The user may now easily recline his body with his back on the platform 58 and his feet respectively upon the steps 106 and 108, steadying himself, if necessary, by grasping one or both of the handles 50, or other parts of the frame structure.

Assuming that the position of the steps 106 and 108 have been previously properly adjustably positioned to place the body in a balanced position with reference to the pivotal support of the body supporting structure B, and that the members 128 and 130 have been properly adjusted to comfortably embrace the ankle areas, the hook end 160, which has preferably been adjusted, will be inserted in the proper opening 144, and the lever 148 swung to its locking position, as shown in full lines in FIG. 6. If the engagement of members 150 and 152 and 128 and 130 feel comfortable, then the lever 148 may be securely locked in its operative position by means of the bail 184. If the engaged portions of the lower body portions are not comfortable, then readjustment should be made in the manner previously described. With the lower body portions thus secured, and with the body in a balanced position, the body supporting structure may be swingably tilted to place the body in an upright or inverted position simply by extending the arms alongside the body or extending them above the head. At the completion of the use period, it is a simple operation to move the bail 184 to a released position and then swing the lever 148 to a position in which the hook 160 may be disconnected, whereupon the user is free to dismount from the step members 106 and 108.

Referring now to FIGS. 11–15, a modified form of the invention is illustrated, which incorporates a number of structural changes for enhancing the basic operational features of the therapeutic device, as previously described.

One of these changes comprises the incorporation of an adjustable pivotal support for the body supporting structure B so as to facilitate adjustment of the spacing distance of the platform 58 with respect to the trunnions 46. This adjustment enables the user to better control the movements of the platform and body balance characteristics during use. As the distance of the platform from the trunnions is increased, the greater will be the tendency of the platform to assume a horizontal position, and as the distance is decreased, the greater will be the tendency of the platform to assume a vertical position.

More specifically, as shown in FIGS. 11 and 12, the legs of the supporting A-frame are pivotally interconnected in each case by a pivot 200 to provide a scissor-connection such that the upper ends coact to form unpwardly opening notches 202 adapted to supportingly receive the side trunnions 46. The extent of opening of the leg structures is limited by a chain 204.

As best seen in FIG. 12, the supporting bracket 52 is in this case constructed to provide two interconnectable sections **52*a* and 52*b* respectively. Section 52*a* is fixedly secured to the adjacent side frame of the platform 58 and is constructed to provide spaced apart side walls 206 and 208 which extend downwardly from the body supporting structure and are adapted to receive the section 52*b* of channel configuration therebetween. The side walls of this channel are provided in their lower end portions with a series of longitudinally spaced apart side wall edge notches 210 which are in transverse alignment. The side walls 206 and 208 adjacent their lower ends are interconnected by a bolt 212 which is adapted to seat in the notches at the respective adjusted positions of the bracket. The bracket 52 may be adjusted to vary the spacing of the platform 58 with respect to the trunnion 46 by tilting the bracket to an angular position as shown in phantom lines in FIG. 12, whereupon the bracket may be shifted to place the bolt 212 in the appropriate notches, and upon moving the bracket section back to its alignment with the fixed section 52*a*; the platform may be suspended in its adjusted position. Each trunnion is retained longitudinally in its operative position by a pair of spaced annular flanges 213**.

The sliding frame structure 92 has also been structurally modified to facilitate its adjustments along the central frame member 76.

As best shown in FIGS. 13, 14 and 15, the outermost end portion of the rectangular tubular frame member 76 has its bottom wall removed together with the lower portion of each side wall, and an inner channel portion 214 secured therein as by welding in a position so that its side walls 216 will extend substantially to the bottom wall of the frame member 76. The side walls 216 are formed with longitudinally spaced semicircular notches 218 which are in transverse alignment.

The sliding frame structure 92 in the modified arrangement comprises an upper U-shaped channel 220 and a lower U-shaped channel 222, these channels being in confronting relationship with their side walls in overlapping relation. The lower channel 222 has side walls 224 which are bridged in this case by a double bridging wall 226.

The inner end portion of the lower channel 222 has its side walls 224 similarly formed with an elongate generally rectangular opening 228 which has its lowermost edge formed with a series of spaced edge notches 230 which are in transverse alignment and adapted to confrontingly mate with the adjacent notches 218 along the lower edges of the side walls 216.

As shown in FIG. 14, the ankle engaging member 128 and 130 are supporting upon a pair of laterally spaced supporting rods 232 which extend through side windows 234 in the side walls of the upper channel 220, and the rectangular openings 228 in positions where they may be clampingly engaged between the notches 218 and 230. The rods 232 are retained against endwise movement by suitable snap rings 236 placed on opposite sides of the side walls of the upper channel 220.

As will be seen in FIG. 15, the steps 106 and 108 are comprised by an elongate bolt 238 and a pair of suitable tubular sleeve members 240 positioned on opposite sides of the side walls of the upper channel 220. As shown in FIG. 13, the bolt 238 extends through the aligned side openings, as generally indicated at 242, in the side walls of the upper channel 220 and the side walls of the lower channel 222. As thus arranged, the bolt 238 will be clampingly engaged between the double bridging wall 226 and the edge notches 218 at the adjusted position of the frame structure 92.

For clampingly securing the frame structure 92 in the desired adjusted position longitudinally of the frame member 76, a clamping cam member 244 is rotatably supported on the side walls of the upper channel member 220 by means of a supporting bolt 246. Manual actuation of the cam 244 is accomplished by means of an elongate rod handle 248 which is arranged to assume a substantially parallel position along the bottom or bridging wall of the lower channel member 222, when the cam is in a fully clamping position. At this position, the handle is arranged to extend through a slot 250 of a fixed bracket 251. A spring-urged latch member 252 is slidably mounted on the outermost end of the handle 248 for sliding movement, the latch member being normally urged towards a latching position by a compression spring 254, one end of this spring bearing against a nut 256 and its other end against the latch member. Upon release, the handle 248 may be freely swung in a clockwise direction to actuate the cam 244 to a position which will permit the downward movement of the lower channel member 222 to a position which will permit adjusting movements of the frame structure 92 longitudinally of the frame member 76, as well as slight adjustment of the positions of the rods 232 in the notches 230, if desired. When the proper adjustment is obtained, the cam 244 is moved to its clamping position and the handle 248 latched to the bracket 251.

Preferably, the upper channel member 220 is supported upon appropriate spacer pads as indicated at 258. As in the case of the structure previously described, the hook 160 is similarly arranged to be selectively inserted into one of the openings 144 of the upper channel member 220. In the modified arrangement, however, it will be seen that the adjacent upper wall of the frame member 76 is provided with a series of openings 260 which have the same spacing as the openings 144 and with which the openings 260 are aligned during adjusting movements of the frame structure 92. Thus, the hook 160 extends through aligned openings 144 and 260 at the adjusted position to releasably lock the frame structure 92 against movement on the frame member 76.

The structure and configuration of the ankle embracing members 128, 130, 150 and 152 has been changed in the modified structure. Basically, each of these members preferably comprises a U-shaped support of metal which is arranged to be supported against tilting movement on a pair of spaced supporting rods. In the case of the members 128 and 130, the U-shaped support, as indicated at 262, is shown as having parallel side walls which are apertured to receive the rods 232 therethrough. The support 262 mounts a pair of spaced inner liners 264 of an elastomeric or other suitable material, these liners having a generally arcuate configuration and being formed with confronting inner surfaces which converge towards a bridging cushion member 266 of a suitable sponge-like material.

In the case of the members 150 and 152, a U-shaped support 268 is constructed of a spring material. The support is constructed to provide diverging side walls which are appropriately provided with triangularly shaped openings 270 for the reception of supporting rods 272 therethrough, these rods being fixedly supported between their ends by the lever member 148. The support 268 has inner liners 274 of elastomeric or other suitable material, and which are connected by a bridging web 276. Bridging cushion members 278 are similarly provided. The spring characteristic of the U-shaped support 268 normally urges the side walls away from each other into a clamped position with respect to the rods 272. However, by manually moving the side walls towards each other, the support may be unclamped with respect to the rods 272 and movably adjusted thereon to a desired position and reclamped simply by releasing the side walls.

The invention and its attendant advantages will be understood from the foregoing description, and it will be apparent that various changes may be made in the form, construction and arrangement of the parts of the invention without departing from the spirit and scope thereof or sacrificing its material advantages, the arrangements hereinbefore described being merely by way of example. It is not wished to be restricted to the specific form shown or uses mentioned except as defined in the accompanying claims.

I claim:

1. In a therapeutic device for the human body in which a main frame pivotally mounts a body supporting structure for longitudinal tilting movements, said structure having an upper body supporting portion and a lower body supporting portion, the lower body supporting portion being connected with the upper body supporting portion by an elongated central frame member, the improvement comprising:

first means carried by the lower body supporting portion positioned to extend under each foot and form a support to limit endwise movement of the body in a downward direction, when the body supporting structure is tilted so as to elevate the head of a body thereon above a horizontal position;

second means carried by the lower body supporting portion positioned and operative to embrace each ankle area and adjacent foot instep area, and form a support to limit endwise movement of the body in an opposite downward direction, when the body supporting structure is tilted so as to lower the head of a body thereon below a horizontal position;

said second means carried by the lower body supporting portion for embracing the adjacent foot instep area including an elongated lever having a lower and an outer end, the lower end of said lever being adapted for detachably engaging and pivotally supporting said elongated lever with respect to the lower body supporting portion; and means adapted for intercoupling said lever near its outer end with the lower body supporting portion for retaining said lever in an engaged and locked position.

2. In a therapeutic device for the human body in which a main frame pivotally mounts a body supporting structure for longitudinal tilting movements, said structure having an upper body supporting portion and a lower body supporting portion, the improvement comprising:

first means carried by the lower body supporting portion positioned to extend under each foot and form a support to limit endwise movement of the body in a downward direction, when the body supporting structure is tilted so as to elevate the head of a body thereon above a horizontal position;

second means carried by the lower body supporting portion positioned and operative to embrace each ankle area and adjacent foot instep area, and form a support to limit endwise movement of the body in an opposite downward direction, when the body supporting structure is tilted so as to lower the head of a body thereon below a horizontal position;

an elongated central frame member interconnected between the upper body supporting portion and the lower body supporting portion;

a frame structure mounted on said central frame member for sliding adjusting movements therealong;

said second means comprises a pair of confronting members for embracing each ankle area and adjacent instep area;

said pair of confronting members being supported on said sliding frame structure for relative positioning adjustments, and for independent relative adjustments with respect to said first means;

one of said pair of confronting members being adjustably supported for movement toward and away from said first means to selective operative positions;

the other of said pair of confronting members being carried by a support that is releasably connectible with said sliding frame structure and said elongated central frame member;

the releasably connectable support for said other of said pair of confronting members comprises an elongated lever a laterally offset hook member is mounted at the outer end of said lever;

a series of openings in spaced relation longitudinally extend along said sliding frame structure for selectively receiving said hook member, and for forming a connection enabling swinging movement of said lever to an operative position extending generally in parallel spaced relation along said central frame; and means releasably latches said lever in said operative position.

3. A therapeutic device according to claim 2, in which:

said latching means comprises a bail member supported for sliding movements on said central frame member, said bail having a looped end positioned for endwise reception of the lever end.

4. A therapeutic device according to claim 2, in which:

mounting means adjustably supports said hook, and is manually operable to increase and decrease the extent of hook offset to thereby vary the operative spaced relationship between said pair of confronting members of said second means.

5. In a therapeutic device for the human body in which a main frame pivotally mounts a body supporting structure for longitudinal tilting movements, said structure having an upper body supporting portion and a lower body supporting portion, the improvement comprising:

first means carried by the lower body supporting portion positioned to extend under each foot and form a support to limit endwise movement of the body in a downward direction, when the body supporting structure is tilted so as to elevate the head of a body thereon above a horizontal position;

second means carried by the lower body supporting portion positioned and operative to embrace each ankle area and adjacent foot instep area, and form a support to limit endwise movement of the body in an opposite downward direction, when the body supporting structure is tilted so as to lower the head of a body thereon below a horizontal position;

said main frame comprises a pair of elevated upwardly opening supporting notches disposed on opposite sides of said upper body supporting portion;

bracket supports are respectively connected with the opposite sides of said upper body supporting portion, said bracket supports having oppositely extending trunnions in spaced relation to said upper body portion and being adapted to respectively seat in said supporting notches; and means for selectively adjusting said brackets to vary the spacing of the upper body supporting portion from said trunnions.

6. A therapeutic device according to claim 5, in which:

each of said brackets comprises adjustably interconnectable sections;

one of said sections being fixedly secured to the upper body supporting portion and including laterally spaced apart side walls;

the other of said sections being formed of a channel member having the trunnions fixedly secured at one end, and side walls having a series of transversely aligned edge opening notches in spaced relation longitudinally along the other end portion of the channel;

and a bolt member extending between the side walls of said one section, and being so positioned as to enable selective positioning in said notches, when said sections are in tilted relation, and being operable to retain the sections in the selected adjustment, when the sections are positioned in axial alignment.

7. In a therapeutic device for the human body in which a main frame pivotally mounts a body supporting structure for longitudinal tilting movements, said structure having an upper body supporting portion and a lower body supporting portion, the improvement comprising:

first means carried by the lower body supporting portion positioned to extend under each foot and form a support to limit endwise movement of the body in a downward direction, when the body supporting structure is tilted so as to elevate the head of a body thereon above a horizontal position;

second means carried by the lower body supporting portion positioned and operative to embrace each ankle area and adjacent foot instep area, and form a support to limit endwise movement of the body in an opposite downward direction, when the body supporting structure is tilted so as to lower the head of a body thereon below a horizontal position;

said second means for each ankle area and instep area comprises a pair of generally confronting members conformed to embrace opposite sides of said ankle area, one of said pair of confronting members additionally embraces the foot instep area;

each of said confronting members comprises a generally U-shaped support mounted against tilting movement on a pair of laterally spaced rod members extending transversely through its side walls;

inner liners of resilient material respectively on the side walls; and inner cushion means in the bottom portion of the U-shaped support extending between the inner liners.

8. A therapeutic device according to claim 7, in which:

the U-shaped member of certain of said embracing members is of a spring material normally operative to urge the side walls away from each other into clamping engagement with its supporting rod members, but upon manual movement of the walls towards each other being clampingly released and enabling adjusting movement of the said embracing member to a different position on said rod members.

9. In a therapeutic device for the human body in which a main frame pivotally mounts a body supporting structure for longitudinal tilting movements, said structure having an upper body supporting portion and a lower body supporting portion, the improvement comprising:

first means carried by the lower body supporting portion positioned to extend under each foot and form a support to limit endwise movement of the body in a downward direction, when the body supporting structure is tilted so as to elevate the head of a body thereon above a horizontal position;

second means carried by the lower body supporting portion positioned and operative to embrace each ankle area and adjacent foot instep area, and form a support to limit endwise movement of the body in an opposite downward direction, when the body supporting structure is tilted so as to lower the head of a body thereon below a horizontal position;

an elongated central frame member interconnected between the upper body supporting portion and the lower body supporting portion;

a frame structure mounted on said central frame member for sliding adjusting movements therealong;

said first means and second means being connected with said sliding frame structure;

means for releasably securing said sliding frame structure in a selected position of adjustment;

said sliding frame structure includes upper and lower U-shaped channel members extending along upper and lower sides of said central frame member, and having their side walls in confronting overlapping relation, the side walls of the upper channel being outwardly of the side walls of the lower channel and projecting beyond the connecting wall of the lower channel;

the releasable securing means comprises a manually rotatable cam supported on the side walls of the upper channel, said cam being engageable with the connecting wall of the lower channel and upon rotation being operative to selectively move said upper and lower channel members into clamped and unclamped positions; and means for releasably latching said cam in the clamped position of said channel members.

10. A therapeutic device according to claim 9, in which:

said elongated central frame member carries longitudinally extended spaced side walls having a series of longitudinally spaced transversely aligned downward opening edge notches;

said first means includes a rod member supported at the outer end of the lower U-shaped channel adapted to seat in a pair of said aligned notches of the central frame member in a clamped adjusted position of said sliding frame structure;

said lower U-shaped channel is formed at its inner end portion with a series of upwardly opening transversely aligned side wall edge notches correspondingly longitudinally spaced and in confronting relation to the notches of the central frame member; and said second means includes ankle embracing members supported on laterally spaced rods adapted to be clampingly engaged between the confronting notches of said lower channel and said central frame member in the clamped adjusted position of said sliding frame structure.

11. In a therapeutic device for the human body in which a main frame pivotally mounts a body supporting structure for longitudinal tilting movements, said structure having an upper body supporting portion and a lower body supporting portion, the improvement comprising:

first means carried by the lower body supporting portion positioned to extend under each foot and form a support to limit endwise movement of the body in a downward direction, when the body supporting structure is tilted so as to elevate the head of a body thereon above a horizontal position;

second means carried by the lower body supporting portion positioned and operative to embrace each ankle area and adjacent foot instep area, and form a support to limit endwise movement of the body in an opposite downward direction, when the body supporting structure is tilted so as to lower the head of a body thereon below a horizontal position;

an elongated central frame member interconnected between the upper body supporting portion and the lower body supporting portion;

a frame structure is mounted on said central frame member for sliding adjusting movements therealong;

said first means are supported at the outer end of said sliding frame structure;

said second means comprises a pair of confronting members for embracing each ankle area and adjacent instep area;

one member of each pair of confronting members is supported at the inner end of said sliding frame structure; and the other member of each pair of confronting members is carried by a detachable support that is releasably connectable with said sliding frame structure and said central frame.

12. A therapeutic device according to claim 11, in which:

the detachable support for said other member of each pair of confronting members comprises an elongate lever with said other of the members positioned adjacent the outer end thereof;

a laterally offset hook member is mounted at the outer end of said lever;

a series of openings extending along an upper portion of said sliding frame structure are adapted to selectively receive said hook member and form a connection enabling swinging movement of said lever to an operative position extending generally in parallel spaced relation along said central frame; and means releasably retains said lever in said operative position.

13. A therapeutic device according to claim 12, in which:

said hook is adjustable to increase and decrease the extent of hook offset.

14. A therapeutic device according to claim 12, in which:

a series of openings in an adjacent surface of said central frame structure are adapted to register with the openings of said sliding frame structure at its respective adjusted positions; and said hook extends through one set of the registered openings to thereby lock the sliding frame structure to the central frame structure at a selected adjusted position.

15. The therapeutic device according to claim 1 wherein said first and second means carried by the lower body supporting portion is adjustably positionable along said elongated central frame member.

16. The therapeutic device according to claim 1 wherein the lower end of said elongated lever includes a hook, said hook being adapted for detachably engaging and pivotally supporting said elongated lever with respect to the lower body supporting portion, the outer end of said elongated lever being adapted to serve as a handle for gripping said lever.

17. The therapeutic device according to claim 1 wherein said means adapted for intercoupling said lever with the lower body supporting portion includes a bail member slidably carried by the elongated central frame member, said bail member being adapted to slip endwise over the outer end of said lever.

18. The therapeutic device according to claim 16 wherein said hook at the lower end of said lever is adjustable with respect to said lever to increase or decrease the extent of hook offset.

* * * * *